United States Patent

Schnabel et al.

[11] Patent Number: 5,861,357
[45] Date of Patent: Jan. 19, 1999

[54] 5-ACYLAMINO-2-ALKOXYCARBONYLPHENYLSULFONYLUREAS AS SELECTIVE HERBICIDES

[75] Inventors: Gerhard Schnabel, Grosswallstadt; Lothar Willms, Hofheim; Klaus Bauer, Hanau; Hermann Bieringer, Eppstein; Christopher Rosinger, Hofheim, all of Germany

[73] Assignee: Hoechst Schering AgrEvo GmbH, Berlin, Germany

[21] Appl. No.: 757,372

[22] Filed: Nov. 27, 1996

[30] Foreign Application Priority Data

Dec. 1, 1995 [DE] Germany ............ 195 44 743.3

[51] Int. Cl.$^6$ .................. A01N 43/20; A01N 43/54; A01N 43/66
[52] U.S. Cl. ........................... 504/212; 504/214
[58] Field of Search ................... 504/212, 214

[56] References Cited

U.S. PATENT DOCUMENTS

| | | | |
|---|---|---|---|
| 4,547,215 | 10/1985 | Wolf | 71/92 |
| 4,632,695 | 12/1986 | Schurter et al. | 71/93 |
| 4,664,695 | 5/1987 | Schurter et al. | 71/92 |
| 4,892,946 | 1/1990 | Levitt | 544/321 |
| 4,981,509 | 1/1991 | Hillemann | 71/93 |
| 5,449,812 | 9/1995 | Schnabel et al. | 560/13 |

FOREIGN PATENT DOCUMENTS

| | | |
|---|---|---|
| 2129528 | 2/1993 | Canada . |
| 0001515 | 4/1979 | European Pat. Off. . |
| 0116518 | 8/1984 | European Pat. Off. . |
| 42 36 902 | 5/1994 | Germany . |
| 43 22 067 | 1/1995 | Germany . |
| 44 15 049 | 11/1995 | Germany . |
| 95/3436 | 2/1996 | South Africa . |
| 95/4463 | 3/1996 | South Africa . |
| 95/4464 | 3/1996 | South Africa . |
| WO 93/16998 | 9/1993 | WIPO . |
| WO 94/10154 | 5/1994 | WIPO . |
| WO 95/32950 | 12/1995 | WIPO . |
| WO 95/32951 | 12/1995 | WIPO . |

*Primary Examiner*—S. Mark Clardy
*Attorney, Agent, or Firm*—Frommer Lawrence & Haug LLP

[57] ABSTRACT

Compounds of the formula (I)

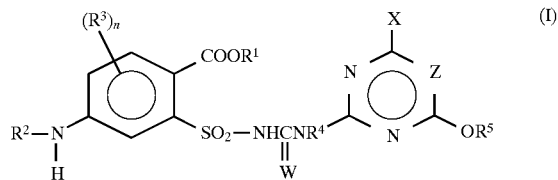

in which

R$^1$ to R$^5$, X, W, n and Z are defined as in claim 1 are particularly suitable for use as selective herbicides in crops of useful plants.

17 Claims, No Drawings

5-ACYLAMINO-2-ALKOXYCARBONYLPHENYLSULFONYLUREAS AS SELECTIVE HERBICIDES

DESCRIPTION

The invention relates to the technical field of herbicides, in particular the use of herbicides for selectively controlling broad-leaved weeds and gramineous weeds in crops of useful plants.

It is known that phenylsulfonylureas which have heterocyclic substituents and carry an amino or a functionalized amino group on the phenyl ring have herbicidal and plant growth-regulating properties; cf. EP-A-1 515, U.S. Pat. No. 4,892,946, U.S. Pat. No. 4,981,509, DE-A-4322067, EP-A-116 518 (=U.S. Pat. No. 4,664,695, U.S. Pat. No. 4,632,695), DE-A-4236902 (WO 94/10154).

However, many of the sulfonylureas mentioned leave something to be desired in respect of selectivity, i.e. they cannot be employed at the application rates necessary for controlling the harmful plants without damaging the crop plants to an adverse degree.

Surprisingly, it has now been found that certain substituted N-(aminophenylsulfonyl)-N'-(pyrimidinyl or triazinyl) ureas are comparatively suitable as selective herbicides.

The present invention relates to the use of compounds of the formula (I)

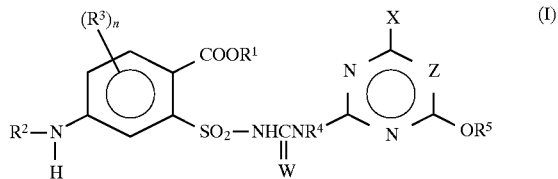

in which
R$^1$ is H, (C$_1$-C$_6$)-alkyl, (C$_2$-C$_6$)-alkenyl, (C$_2$-C$_6$)-alkynyl, (C$_3$-C$_6$)-cycloalkyl, where the last four radicals mentioned are unsubstituted or substituted by one or more radicals from the group consisting of halogen, CN, (C$_1$-C$_3$)-alkoxy, (C$_1$-C$_3$)-haloalkoxy, unsubstituted and substituted (C$_3$-C$_6$)-cycloalkyl, (C$_1$-C$_3$)-alkylthio, (C$_1$-C$_3$)-alkylsulfinyl, (C$_1$-C$_3$)-alkylsulfonyl, unsubstituted phenyl, substituted phenyl, an unsubstituted heterocyclic radical and a substituted heterocyclic radical and, in the case of cyclic radicals, also (C$_1$-C$_4$)-alkyl and (C$_1$-C$_4$)-haloalkyl, or a heterocyclic radical having 3, 4, 5, 6 or 7 ring atoms and one or more atoms from the group consisting of O, N and S as hetero ring atoms, the radical being unsubstituted or substituted by one or more radicals from the group consisting of halogen, (C$_1$-C$_3$)-alkyl and (C$_1$-C$_3$)-haloalkyl,
R$^2$ is an acyl radical, excluding formyl,
R$^3$ is halogen, (C$_1$-C$_6$)-alkyl, (C$_1$-C$_6$)-alkoxy, (C$_1$-C$_6$)-haloalkyl, (C$_1$-C$_6$)-haloalkoxy, NO$_2$, CN, NH$_2$ or (C$_1$-C$_4$)-mono- or -dialkylamino, and in particular in each case independently of other radicals R$^3$ if n is 2 or 3,
R$^4$ is H or (C$_1$-C$_6$)-alkyl,
R$^5$ is (C$_1$-C$_6$)-alkyl or (C$_1$-C$_6$)-haloalkyl,
X is a halogen atom from the group consisting of F and Cl or halo-(C$_1$-C$_3$)-alkyl,
n is 0, 1, 2 or 3,
W is an oxygen atom or a sulfur atom and
Z is CH or N,
as selective herbicides for controlling harmful plants in crops of useful plants.

Salts of 5-acylamino-2-alkoxycarbonylphenylsulfonylureas have been proposed as herbicides having a potent action in German Patent Application P 4419259.2 (WO 95/32951). The salts are prepared from the corresponding free sulfonylureas by reaction with a base. Some of the free sulfonylureas which are used according to German Patent Application P 4419259.2 (WO 95/32951) as intermediate products for the preparation of the herbicidal salts are identical to abovementioned compounds of the formula (I). However, it was not known to date that the compounds of the formula (I) themselves are particularly suitable as selective herbicides.

5-Formylamino-2-alkoxycarbonylphenylsulfonylureas have already been proposed as selective herbicides having a potent action in German Patent Application No. 19510078.6 (WO 95132950).

In the formula (I) mentioned and all the formulae below, the alkyl, alkoxy, haloalkyl, haloalkoxy, alkylamino and alkylthio radicals and the corresponding unsaturated and/or substituted radicals can in each case be straight-chain or branched in the carbon skeleton. Unless specifically stated, the lower carbon skeletons, for example having 1 to 4 carbon atoms, or in the case of unsaturated groups having 2 to 4 carbon atoms, are preferred for these radicals. Alkyl radicals, including in the composite meanings, such as alkoxy, haloalkyl and the like, are, for example, methyl, ethyl, n- or i-propyl, n-, i-, t- or 2-butyl, pentyl radicals, hexyl radicals, such as n-hexyl, i-hexyl and 1,3-dimethylbutyl, or heptyl radicals, such as n-heptyl, 1-methylhexyl and 1,4-dimethylpentyl; alkenyl and alkynyl radicals have the meaning of the possible unsaturated radicals corresponding to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; and alkynyl is, for example, propargyl, but-2-yn-1-yl, but-3-yn-1-yl and 1-methylbut-3-yn-1-yl.

Halogen is, for example, fluorine, chlorine, bromine or iodine. Haloalkyl, -alkenyl and -alkynyl are alkyl, alkenyl or alkynyl, respectively, which are partly or completely substituted by halogen, preferably by fluorine, chlorine and/or bromine, in particular by fluorine or chlorine, for example CF$_3$, CHF$_2$, CH$_2$F, CF$_3$CF$_2$, CH$_2$FCHCl, CCl$_3$, CHCl$_2$ or CH$_2$CH$_2$Cl; haloalkoxy is, for example, OCF$_3$, OCHF$_2$, OCH$_2$F, CF$_3$CF$_2$O, OCH$_2$CF$_3$ and OCH$_2$CH$_2$Cl; the corresponding applies to haloalkenyl and other radicals substituted by halogen.

A heterocyclic radical or ring can be saturated, unsaturated or heteroaromatic; it contains one or more hetero ring atoms, preferably from the group consisting of N, O and S; preferably, it is 5- or 6-membered and contains 1, 2 or 3 hetero ring atoms. The heterocyclic radical can be, for example, a heteroaromatic radical or ring (hetaryl), such as, for example, a mono-, bi- or polycyclic aromatic system, in which at least 1 ring contains one or more heteroatoms, for example pyridyl, pyrimidinyl, pyridazinyl, pyrazinyl, thienyl, thiazolyl, oxazolyl, furyl, pyrrolyl, pyrazolyl and imidazolyl, or it is a partially hydrogenated radical, such as oxiranyl, pyrrolidyl, piperidyl, piperazinyl, dioxolanyl, morpholinyl or tetrahydrofuryl. Possible substituents for a substituted heterocyclic radical are the substituents mentioned below, and in addition also oxo. The oxo group can also occur on the hetero ring atoms which can exist in different oxidation states, for example in the case of N and S.

Substituted radicals, such as substituted hydrocarbon radicals, for example substituted alkyl, alkenyl, alkynyl, aryl, phenyl and benzyl, or substituted hetaryl, are, for example, a substituted radical derived from the unsubstituted parent substance, the substituents being, for example, one or more, preferably 1, 2 or 3, radicals from the group consisting of halogen, alkoxy, haloalkoxy, alkylthio, hydroxyl, amino, nitro, cyano, azido, alkoxycarbonyl, alkylcarbonyl, formyl, carbamoyl, mono- and dialkylaminocarbonyl, substituted amino, such as acylamino and mono- and dialkylamino, and alkylsulfinyl, haloalkylsulfinyl, alkylsulfonyl, haloalkylsulfonyl and, in the case of cyclic radicals, also alkyl and haloalkyl, as well as saturated aliphatic radicals corresponding to the saturated hydrocarbon-containing radicals mentioned, such as alkenyl, alkynyl, alkenyloxy, alkynyloxy and the like. In the case of radicals with carbon atoms, those having 1 to 4 carbon atoms, in particular 1 or 2 carbon atoms, are preferred. Substituents from the group consisting of halogen, for example fluorine and chlorine, ($C_1$-$C_4$)-alkyl, preferably methyl or ethyl, ($C_1$-$C_4$)-haloalkyl, preferably trifluoromethyl, ($C_1$-$C_4$)-alkoxy, preferably methoxy or ethoxy, ($C_1$-$C_4$)-haloalkoxy, nitro and cyano, are as a rule preferred. The substituents methyl, methoxy and chlorine are particularly preferred here.

Optionally substituted phenyl is preferably phenyl which is unsubstituted or mono- or polysubstituted, preferably up to three times, by identical or different radicals from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy and nitro, for example o-, m- and p-tolyl, dimethylphenyl radicals, 2-, 3- and 4-chlorophenyl, 2-, 3- and 4-trifluoro- and -trichlorophenyl, 2,4-, 3,5-, 2,5- and 2,3-dichlorophenyl and o-, m- and p-methoxyphenyl.

An acyl radical is the radical of an organic acid, for example the radical of a carboxylic acid and radicals of acids derived therefrom, such as the thiocarboxylic acid, optionally N-substituted iminocarboxylic acids, or the radical of carbonic acid monoesters, optionally N-substituted carbamic acid, sulfonic acids, sulfinic acids, phosphonic acids and phosphinic acids. Acyl is, for example, formyl, alkylcarbonyl, such as [($C_1$-$C_4$)-alkyl]carbonyl, phenylcarbonyl, in which the phenyl ring can be substituted, for example as shown above for phenyl, or alkoxycarbonyl, phenyloxycarbonyl, benzyloxycarbonyl, alkylsulfonyl, alkylsulfinyl, N-alkyl-1-iminoalkyl and other radicals of organic acids.

The invention also relates to all the stereoisomers included by the formula (I) and mixtures thereof. Such compounds of the formula (I) contain one or more asymmetric carbon atoms or else double bonds, which are not shown separately in the formula (I). The possible stereoisomers defined by their specific spatial form, such as enantiomers, diastereomers and Z and E isomers, are all included in the formula (I) and can be obtained from mixtures of the stereoisomers by customary methods or else prepared by stereoselective reactions in combination with the use of stereochemically pure starting substances.

Uses according to the invention which are of particular interest are those with compounds of the formula (I) in which $R^1$ is ($C_1$-$C_6$)-alkyl, ($C_2$-$C_6$)-alkenyl, ($C_2$-$C_6$)-alkynyl, ($C_3$-$C_6$)-cycloalkyl, ($C_4$-$C_8$)-cycloalkyl-($C_1$-$C_2$)-alkyl, phenyl-($C_1$-$C_6$)-alkyl, where each of the last six radicals mentioned is unsubstituted or substituted by one or more radicals from the group consisting of halogen, such as F, Cl, Br and I, CN, $OCH_3$, $OC_2H_5$, $OCF_3$, $SO_2CH_3$ and, in the case of cyclic radicals, also ($C_1$-$C_3$)-alkyl, or a radical of the formulae $A_1$ to $A_7$, in particular $A_1$, $A_2$ or $A_3$,

 (A$_1$)

-continued

 (A$_2$)

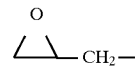 (A$_3$)

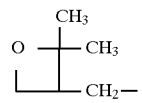 (A$_4$)

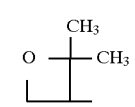 (A$_5$)

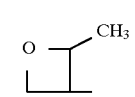 (A$_6$)

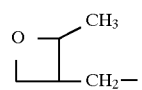 (A$_7$)

$R^2$ is CO—$R^6$, CO—$OR^7$, CO—$NR^8R^9$ or $SO_2$—$R^{10}$,
$R^3$ is halogen, ($C_1$-$C_3$)-alkyl, ($C_1$-$C_3$)-alkoxy, ($C_1$-$C_3$)-haloalkyl, ($C_1$-$C_3$)-haloalkoxy, $NO_2$, CN, $NH_2$, $NHCH_3$ or $N(CH_3)_2$,
$R^4$ is H or ($C_1$-$C_3$)-alkyl,
$R^5$ is ($C_1$-$C_3$)-alkyl or ($C_1$-$C_3$)-haloalkyl,
$R^6$ is ($C_1$-$C_6$)-alkyl, ($C_2$-$C_6$)-alkenyl, ($C_2$-$C_6$)-alkynyl, ($C_3$-$C_6$)-cycloalkyl, where each of the last four radicals mentioned is unsubstituted or substituted by one or more radicals from the group consisting of halogen, CN, ($C_1$-$C_4$)-alkoxy, ($C_1$-$C_4$)-haloalkoxy, mono-($C_1$-$C_4$)-alkylamino, di-($C_1$-$C_4$)-alkylamino, ($C_1$-$C_4$)-alkylsulfonyl, ($C_1$-$C_4$)-alkylsulfinyl, [($C_1$-$C_4$)-alkoxy]carbonyl, aminocarbonyl, mono-[($C_1$-$C_4$)-alkyl]aminocarbonyl, di-[($C_1$-$C_4$)-alkyl]aminocarbonyl, unsubstituted phenyl and substituted phenyl, or phenyl, which is unsubstituted or substituted,
$R^7$ is a radical from the group of radicals possible for $R^6$,
$R^8$ and $R^9$ independently of one another are H, ($C_1$-$C_6$)-alkyl, ($C_2$-$C_6$)-alkenyl or ($C_2$-$C_6$)-alkynyl, where each of the last three radicals mentioned is unsubstituted or substituted by one or more radicals from the group consisting of halogen, such as F, Cl and Br, CN, ($C_1$-$C_4$)-alkoxy, ($C_1$-$C_4$)-haloalkoxy, mono-($C_1$-$C_4$)-alkylamino, di-($C_1$-$C_4$)-alkylamino, ($C_1$-$C_4$)-alkylsulfonyl, ($C_1$-$C_4$)-alkylsulfinyl, [($C_1$-$C_4$)-alkoxy]carbonyl, aminocarbonyl, mono-($C_1$-$C_4$)-alkylaminocarbonyl and di-[($C_1$-$C_4$)-alkyl]aminocarbonyl, or
$R^8$ and $R^9$, together with the N atom bonded to them, is an unsubstituted or substituted heterocyclic ring of four to eight ring atoms which, including the substituents, contains up to 18 carbon atoms, preferably up to 12 carbon atoms,
$R^{10}$ is ($C_1$-$C_5$)-alkyl or ($C_2$-$C_5$)-alkenyl, where each of the last two radicals mentioned is unsubstituted or substituted by one or more radicals from the group consisting of halogen, ($C_1$-$C_4$)-alkoxy, ($C_1$-$C_4$)-haloalkoxy, mono-($C_1$-$C_4$)-alkylamino and di-($C_1$-$C_4$)-alkylamino,
n is 0 or 1, preferably 0,
W is O,
X is F, Cl or $CF_3$, preferably Cl, and
Z is CH or N, preferably CH.
Preferred uses according to the invention are those with compounds of the formula (I) in which $R^1$ is $(C_1\text{-}C_6)$-alkyl, $(C_2\text{-}C_6)$-alkenyl, $(C_2\text{-}C_6)$-alkynyl, $(C_3\text{-}C_6)$-cycloalkyl, $(C_3\text{-}C_6)$-cycloalkyl-$(C_1\text{-}C_2)$alkyl or phenyl-$(C_1\text{-}C_6)$-alkyl, where each of the last six radicals mentioned is unsubstituted or substituted by one or more radicals from the group consisting of halogen, such as F, Cl, Br and I, CN, $OCH_3$, $OC_2H_5$, $OCF_3$, $SO_2CH_3$ and, in the case of cyclic radicals, also $(C_1\text{-}C_3)$-alkyl, or a radical of the formulae $A_1$ to $A_7$, in particular $A_1$, $A_2$ or $A_3$,

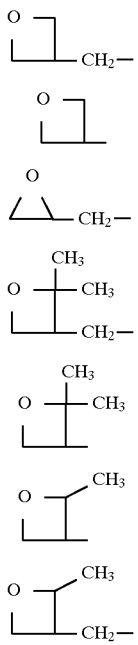

$R^2$ is $CO\text{—}R^6$, $CO\text{—}OR^7$, $CO\text{—}NR^8R^9$ or $SO_2\text{—}R^{10}$,
$R^3$ is halogen, $CH_3$, $C_2H_5$, $OCH_3$, $OC_2H_5$, $CF_3$, $CCl_3$, $OCF_3$, $OCHF_2$ or $N(CH_3)_2$,
$R^4$ is H or methyl,
$R^5$ is methyl, ethyl or $(C_1\text{-}C_2)$-haloalkyl,
$R^6$ is $(C_1\text{-}C_6)$-alkyl, $(C_2\text{-}C_6)$-alkenyl, $(C_2\text{-}C_6)$-alkynyl, $(C_3\text{-}C_6)$-cycloalkyl, where each of the last four radicals mentioned is unsubstituted or substituted by one or more radicals from the group consisting of F, Cl, Br, I, CN, $OCH_3$, $OCF_3$, $N(CH_3)_2$, $SO_2CH_3$, $CO_2CH_3$, $CON(CH_3)_2$ and phenyl,
or phenyl, which is unsubstituted or substituted up to three times by identical or different radicals from the group consisting of halogen, $CH_3$, $C_2H_5$, $OCH_3$, $OC_2H_5$, $CF_3$, $C_2H_5Cl$, $OCHF_3$ and $OCHF_2$,
$R^7$ is a radical from the group of radicals possible for $R^6$,
$R^8$ and $R^9$ independently of one another are H, $(C_1\text{-}C_6)$-alkyl, $(C_2\text{-}C_6)$-alkenyl or $(C_2\text{-}C_6)$-alkynyl, where each of the last three radicals mentioned is unsubstituted or substituted by one or more radicals from the group consisting of F, Cl, Br, CN, $OCH_3$, $OCF_3$, $N(CH_3)_2$, $SO_2CH_3$, $CO_2CH_3$ and $CON(CH_3)_2$, and
$R^{10}$ is $(C_1\text{-}C_4)$-alkyl or $(C_1\text{-}C_4)$-haloalkyl.

Particularly preferred uses according to the invention are those with compounds of the formula (I), in which
$R^1$ is $(C_1\text{-}C_4)$-alkyl, preferably methyl or ethyl,
$R^2$ is $CO\text{—}R^6$, preferably $CO\text{—}CH_3$, $CO\text{—}CH_2CH_3$, cyclopropylcarbonyl, isopropylcarbonyl or t-butylcarbonyl, in particular $CO\text{—}CH_3$, or
$R^2$ is $CO\text{—}OR^7$, preferably $COOCH_3$, $COOC_2H_5$ and $COOCH_2CH_2Cl$, or
$R^2$ is $CO\text{—}NR^8R^9$, preferably $CONH_2$, $CONHCH_3$, $CO\text{-}NH\text{-}C_2H_5$ or $CON(CH_3)_2$, or
$R^2$ is $SO_2\text{—}R^{10}$, preferably $SO_2CH_3$, $SO_2C_2H_5$, $SO_2CH_2F$ or $SO_2CH_2Cl$.

The compounds of the formula (I) can be prepared by processes described in the abovementioned literature or by analogous processes, in particular by the processes described for formyl derivatives in German Patent Application No. 19510078.6 (WO 95/32950). Instead of the formyl radical, other acyl radicals are then used, and the compounds are prepared using acylating agents which are customary for the acyl radicals in question.

The compounds of the formula (I) according to the invention have an excellent herbicidal activity against a broad spectrum of economically important mono- and dicotyledon harmful plants. Perennial weeds which are difficult to control and shoot from rhizomes, root stock or other permanent organs are also readily attacked by the active compounds. It is irrelevant here whether the substances are applied by the presowing, preemergence or postemergence method. Some representatives of monocotyledon and dicotyledon weed flora which can be controlled by the compounds according to the invention may be mentioned specifically by way of example without a limitation to certain species being intended by the naming of these.

On the part of the monocotyledon species of weeds, for example, Avena, Lolium, Alopecurus, Phalaris, Echinochloa, Digitaria, Setaria and Cyperus species from the annual group and, on the part of the perennial species, Agropyron, Cynodon, Imperata and Sorghum and also perennial Cyperus species are readily attacked. In the case of dicotyledon species of weeds, the action spectrum extends to species such as, for example, Galium, Viola, Veronica, Lamium, Stellaria, Amaranthus, Sinapis, Ipomoea, Matricaria, Abutilon and Sida on the annual side, and Convolvulus, Cirsium, Rumex and Artemisia in the case of perennial weeds.

Weeds which occur under the specific growing conditions in rice, such as, for example, Sagittaria, Alisma, Eleocharis, Scirpus and Cyperus, are likewise controlled outstandingly by the active compounds according to the invention.

If the compounds according to the invention are applied to the soil surface before germination, either the emergence of the weed seedlings is prevented completely or the weeds grow to the cotyledon stage but then stop their growth and finally die completely at the end of three to four weeks.

If the active compounds are applied to the green parts of plants by the postemergence method, a drastic stop in growth likewise occurs very rapidly after the treatment and the weed plants remain in the growth stage existing at the time of application or die completely after a certain period of time, so that weed competition, which is harmful to the crop plants, is eliminated very early and lastingly in this manner.

Although the compounds according to the invention have an excellent herbicidal activity against monocotyledon and dicotyledon weeds, crop plants of economically important crops, such as, for example, wheat, barley, rye, rice, maize, sugar beet, cotton and soya, are harmed only insignificantly, or not at all. In direct comparsion with structurally close sulfonylurea herbicides from the 4,6-dimethoxy- or 4-methoxy-6-methylpyrimidinyl or -triazinyl series or with other aminophenylsulfonyl-ureas, the compounds (I) show surprisingly improved selectivities. For these reasons, the present compounds are particularly suitable for selective control of undesirable plant growth in agricultural crop plantations.

The substances according to the invention furthermore have outstanding growth-regulating properties in crop plants. They intervene in the endogenous metabolism of the plants in a regulatory manner and can therefore be employed for exerting controlled influence over plant contents and for facilitating harvesting, for example by inducing desiccation and stunted growth. They are, furthermore, also suitable for general control and inhibition of undesirable vegetative growth without killing the plants at the same time. Inhibition of vegetative growth plays a major role in many mono- and dicotyledon crops, since lodging can be reduced or prevented completely by this means.

The compounds to be employed according to the invention can be used in the customary formulations in the form of wettable powders, emulsifiable concentrates, sprayable solutions, dusting powders or granules. The invention therefore also relates to herbicidal and plant growth-regulating compositions which comprise the compounds of the formula (I).

The compounds of the formula (I) can be formulated in various ways, depending on the biological and/or chemico-physical parameters which exist. Suitable formulation possibilities are, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusting powders (DP), dressings, granules for application by scattering and to the soil, granules (GR) in the form of microgranules, sprayed granules, absorption granules and adsorption granules, water-dispersible granules (WG), water-soluble granules (SG), ULV formulations, microcapsules and waxes.

These individual types of formulation are known in principle and are described, for example, in: Winnacker-Kuchler, "Chemische Technologie" [Chemical Technology], Volume 7, C. Hauser Verlag Munich, 4th edition 1986, Wade van Valkenburg, "Pesticide Formulations", Marcel Dekker, N.Y., 1973; K. Martens, "Spray Drying" Handbook, 3rd edition 1979, G. Goodwin Ltd. London.

The necessary formulation auxiliaries, such as inert materials, surfactants, solvents and further additives, are likewise known and are described, for example, in: Watkins, "Handbook of Insecticide Dust Diluents and Carriers", 2nd edition, Darland Books, Caldwell N.J., H.v. Olphen, "Introduction to Clay Colloid Chemistry"; 2nd edition, J. Wiley & Sons, N.Y.; C. Marsden, "Solvents Guide"; 2nd edition, Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag Munich, 4th edition 1986.

Combinations with other substances having a pesticidal action, such as, for example, insecticides, acaricides, other herbicides, fungicides, safeners, fertilizers and/or growth regulators can also be prepared on the basis of these formulations, for example in the form of a ready-to-use formulation or as a tank mix.

Wettable powders are preparations which are uniformly dispersible in water and which, alongside the active compound, and in addition to a diluent or inert substance, also comprise surfactants of an ionic and/or nonionic nature (wetting agents, dispersing agents), for example polyoxyethylated alkylphenols, polyoxethylated fatty alcohols, polyoxethylated fatty amines, fatty alcohol polyglycol ether sulfates, alkanesulfonates, alkylbenzenesulfonates, sodium ligninsulfonate, sodium 2,2'-dinaphthylmethane-6,6'-disulfonate, sodium dibutyinaphthalenesulfonate or alternatively sodium oleoylmethyltauride. To prepare the wettable powders, for example, the herbicidal active compounds are finely ground in customary apparatus, such as hammer mills, blast mills and air jet mills, and are mixed with the formulating auxiliaries at the same time or subsequently.

Emulsifiable concentrates are prepared by dissolving the active compound in an organic solvent, for example butanol, cyclohexanone, dimethylformamide, xylene or also higher-boiling aromatics or hydrocarbons or mixtures of organic solvents, with the addition of one or more surfactants of an ionic and/or nonionic nature (emulsifiers). Emulsifiers which can be used are, for example: calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, alkyl polyethers, sorbitan esters, such as, for example, sorbitan fatty acid esters, or polyoxyethylene sorbitan esters, such as, for example, polyoxyethylene sorbitan fatty acid esters.

Dusting powders are obtained by grinding the active compound with finely divided solid substances, for example talc, naturally occurring clays, such as kaolin, bentonite and pyrophyllite, or diatomaceous earth.

Suspension concentrates can be water- or oil-based. They can be prepared, for example, by wet grinding using commercially available bead mills and, if appropriate, with the addition of surfactants, such as are already listed above, for example, for the other types of formulation.

Emulsions, for example oil-in-water emulsions (EW), can be prepared, for example, by means of stirrers, colloid mills and/or static mixers using aqueous organic solvents and, if appropriate, surfactants, such as are already listed above, for example, for the other types of formulation. Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the preparation of fertilizer granules—if desired as a mixture with fertilizers.

Water-dispersible granules are as a rule prepared by the customary processes, such as spray drying, fluidized bed granulation, disk granulation, mixing with high-speed mixers and extrusion without a solid inert material.

The agrochemical formulations as a rule comprise 0.1 to 99% by weight, in particular 0.1 to 95% by weight, of active compound of the formula (I).

In wettable powders, the active compound concentration is, for example, about 10 to 90% by weight, the remainder to make up to 100% by weight comprising customary formulation constituents. In emulsifiable concentrates, the active compound concentration can be about 1 to 90, preferably 5 to 80% by weight. Dust-like formulations comprise 1 to 30, preferably usually 5 to 20% by weight of active compound, and sprayable solutions comprise about 0.05 to 80, preferably 2 to 50% by weight of active compound. In water-dispersible granules, the active compound content partly depends on whether the active compound is present in liquid or solid form and which granulating auxiliaries, fillers and the like are used. In water-dispersible granules, the content of active compound is, for example, between 1 and 95% by weight, preferably between 10 and 80% by weight.

In addition, the active compound formulations mentioned comprise, if appropriate, the particular customary tackifiers, wetting agents, dispersing agents, emulsifiers, penetration agents, preservatives, antifreezes and solvents, fillers, carrier substances and dyestuffs, defoamers, evaporation inhibitors and agents which influence the pH and the viscosity.

Known active compounds such as are described, for example, in Weed Research 26, 441–445 (1986), or "The Pesticide Manual", 10th edition, The British Crop Protection Council and the Royal Society of Chemistry, 1994, England, and literature mentioned therein can be employed as combination partners for the active compounds according to the invention in mixture formulations or in a tank mix. The following active compounds may be mentioned, for example, as herbicides which are known from the literature and can be combined with the compounds of the formula (I) (Note: the compounds are named either by their common name according to the International Organization for Standardization (ISO) or by their chemical name, if appropriate together with a customary code number): acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy]-acetic acid and -acetic acid methyl ester; alachlor; alloxydim; ametryn; amidosulfuron; amitrol; AMS, i.e. ammonium sulfamate; anilofos; asulam; atrazin; aziprotryn; barban; BAS 516 H, i.e. 5-fluoro-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; carbetamide; CDAA, i.e. 2-chloro-N,N-di-2-propenylacetamide; CDEC, i.e. diethyldithiocarbamic acid 2-chloroallyl ester; CGA 184927, i.e. 2-[4-[(5-chloro-3-fluoro-2-pyridinyl)oxy]phenoxy]propanoic acid and the 2-propynyl ester; chlomethoxyfen; chloramben; chlorazifop-butyl, pirifenop-butyl; chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clomazone; clomeprop; cloproxydim; clopyralid; cyanazine; cycloate; cycloxydim; cycluron; cyperquat; cyprazine; cyprazole; 2,4-DB; dalapon; desmedipham; desmetryn; di-allate; dicamba; dichlobenil; dichlorprop; diclofop-methyl; diethatyl; difenoxuron; difenzoquat; diflufenican; dimefuron; dimethachlor; dimethametryn; dimethazone, clomazon; dimethipin; dimetrasulfuron; cinosulfuron; dinitramine; dinoseb; dinoterb; diphenamid; dipropetryn; diquat; dithiopyr; diuron; DNOC; eglinazine-ethyl; EL 177, i.e. 5-cyano-1-(1,1-dimethylethyl)-N-methyl-3H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; F6285, i.e. 1-[5-(N-methylsulfonyl)-amino-2,4-dichlorophenyl]-3-methyl-4-difluoromethyl-1,2,4-triazol-5-one; fenoprop; fenoxan; fenoxaprop-ethyl; fenuron; flamprop-methyl; flazasulfuron; fluazifop and ester derivatives thereof; fluchloralin; flumetsulam; N-[2,6-difluorophenyl]-5-methyl(1,2,4)triazolo[1,5-a]pyrimidine-2-sulfonamide; flumeturon; flumipropyn; fluorodifen; fluoroglycofen-ethyl; fluridone; flurochloridone; fluroxypyr; flurtamone; fomesafen; fosamine; furyloxyfen; glufosinate; glyphosate; halosaten; haloxyfop and ester derivatives thereof; hexazinone; Hw 52, i.e. N-(2,3-dichlorophenyl)-4-(ethoxymethoxy)benzamide; imazamethabenz-methyl; imazapyr; imazaquin; imazethamethapyr; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldymron; metobromuron; metolachlor; metoxuron; metribuzin; metsulfuron-methyl; MH; molinate; monalide; monocarbamide dihydrogen sulfate; monolinuron; monuron; MT 128, i.e. 6-chloro-N-(3-chloro-2-propenyl)-5-methyl-N-phenyl-3-pyridazineamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiazon; oxyfluorfen; paraquat; pebulate; pendimethalin; perfluidone; phenmedipham; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and ester derivatives thereof; propazine; propham; propyzamide; prosulfalin; prosulfocarb; prynachlor; pyrazolinate; pyrazon; pyrazosulfuron-ethyl; pyrazoxyfen; pyridate; quinclorac; quinmerac; quinofop and ester derivatives thereof; quizalofop and ester derivatives thereof; quizalofop-ethyl; quizalofop-p-tefuryl; renriduron; dymron; S 275, i.e. 2-[4-chloro-2-fluoro-5-(2-propynyloxy)phenyl]-4,5,6,7-tetrahydro-2H-indazole; S 482, i.e. 2-[7-fluoro-3,4-dihydro-3-oxo4-(2-propynyl)-2H-1,4-benzoxazin-6-yl]-4,5,6,7-tetrahydro-1H-isoindole-1,3(2H)-dione; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and the methyl ester thereof; sulfometuron-methyl; sulfazuron; flazasulfuron; TCA; tebutam; tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thiazafluron; thifensulfuron-methyl; thiobencarb; tiocarbazil; tralkoxydim; tri-allate; triasulfuron; triazofenamide; tribenuron-methyl; triclopyr; tridiphane; trietazine; trifluralin; trimeturon; vernolate; WL 110547, i.e. 5-phenoxy-1-[3-(trifluoromethyl)phenyl]-1H-tetrazole.

For use, the formulations in the commercially available form are diluted in the customary manner, if appropriate, for example by means of water in the case of wettable powders, emulsifiable concentrates, dispersions and water-dispersible granules, and are then applied to the plants, parts of plants or the agriculturally or industrially used soil on which the plants stand or in which they grow or are present as seeds. Dust-like formulations, soil granules or broadcasting granules and sprayable solutions are usually not diluted further with additional inert substances before use.

The required rake of application of compounds of the formula (I) varies with the outdoor conditions, such as temperature and humidity, the nature of the herbicide used and the like. It can vary within wide limits, for example between 0.001 and 10.0 kg/ha or more of active substance, but is preferably between 0.005 and 5 kg/ha.

USE EXAMPLES

Examples of the compounds of the formula (I) to be employed according to the invention are listed in the following Table 1. The following abbreviations are used in Table 1:

No.=Example number
m.p.=Solidification point (melting point) in 0° C.

Me=Methyl
Et=Ethyl
Pr=$^n$Pr=n-Propyl
$^i$Pr=i-Propyl
$^c$Pr=Cyclopropyl
$^n$Bu=n-Butyl
(d)=decomposition

TABLE 1

Structure:

$$R^2\text{-NH-}\underset{6}{\underset{5}{\overset{4}{\overset{3}{\phantom{C}}}}}\text{-benzene-}\underset{1}{\overset{2}{\phantom{C}}}(COOR^1)(SO_2NHC(O)NR^4\text{-pyrimidine}(X)(Z)(OR^5))$$

with $(R^3)_n$ on ring

| No. | R$^1$ | R$^2$ | (R$^3$)$_n$ | R$^4$ | R$^5$ | X | Z | m.p. [°C.] |
|---|---|---|---|---|---|---|---|---|
| 1 | Me | SO$_2$Me | — | H | Me | Cl | CH | |
| 2 | Et | " | — | H | Me | Cl | CH | |
| 3 | $^n$Pr | " | — | H | Me | Cl | CH | |
| 4 | Me | CO—$^c$Pr | — | H | Me | Cl | CH | |
| 5 | Me | " | — | Me | Me | Cl | CH | |
| 6 | Me | " | — | H | CHF$_2$ | Cl | CH | |
| 7 | Me | " | — | H | Me | F | CH | |
| 8 | Et | " | — | H | Me | Cl | CH | |
| 9 | $^n$Pr | " | — | H | Me | Cl | CH | |
| 10 | Me | CO—Me | — | H | Me | Cl | CH | |
| 11 | Me | CO—Me | — | Me | Me | Cl | CH | |
| 12 | Me | COOMe | — | H | Me | Cl | CH | |
| 13 | Et | COOMe | — | H | Me | Cl | CH | |
| 14 | $^n$Pr | COOMe | — | H | Me | Cl | CH | |
| 15 | $^i$Pr | COOMe | — | H | Me | Cl | CH | |
| 16 | Me | COOEt | — | H | Me | Cl | CH | |
| 17 | Me | COOEt | — | Me | Me | Cl | CH | |
| 18 | Et | COOEt | — | H | Me | Cl | CH | |
| 19 | $^n$Pr | COOEt | — | H | Me | Cl | CH | |
| 20 | $^i$Pr | COOEt | — | H | Me | Cl | CH | |
| 21 | oxiranylmethyl (H$_2$C—O—CH—CH$_2$) | COOEt | — | H | Me | Cl | CH | |
| 22 | oxiranylmethyl | COOMe | — | H | Me | Cl | CH | |
| 23 | oxiranylmethyl | SO$_2$Me | — | H | Me | Cl | CH | |
| 24 | $^n$Bu | SO$_2$Me | — | H | Me | Cl | CH | |
| 25 | Me | COCH$_2$Cl | — | H | Me | Cl | CH | |
| 26 | Me | COCHCl$_2$ | — | H | Me | Cl | CH | |
| 27 | Me | COCF$_3$ | — | H | Me | Cl | CH | |
| 28 | Me | COCH$_2$OMe | — | H | Me | Cl | CH | |
| 29 | CH$_2$CH=CH$_2$ | SO$_2$CH$_2$F | — | H | Me | Cl | CH | |
| 30 | CH$_2$CH=CH$_2$ | COOMe | — | H | Me | Cl | CH | |
| 31 | CH$_2$CH=CH$_2$ | COCH$_3$ | — | H | Me | Cl | CH | |
| 32 | CH$_2$CH=CH$_2$ | " | — | H | Me | F | CH | |
| 33 | oxiranylmethyl | CO—Me | — | H | Me | Cl | CH | |
| 34 | oxiranylmethyl | CO—Me | — | H | Me | F | CH | |
| 35 | oxiranylmethyl | COOMe | — | H | Me | F | CH | |
| 36 | oxiranylmethyl | COOEt | — | H | Me | F | CH | |
| 37 | oxetanylmethyl (CH$_2$-O-CH$_2$-CH$_2$) | COOEt | — | H | Me | F | CH | |
| 38 | oxetanylmethyl | COOMe | — | H | Me | Cl | CH | |
| 39 | cyclopropylmethyl | CO—Me | — | H | Me | Cl | CH | |
| 40 | Me | CO—Me | — | H | Me | Cl | N | |
| 41 | CH$_2$CH$_2$Cl | CO—Me | — | H | Me | Cl | N | |
| 42 | CH$_2$CH$_2$OMe | CO—Me | — | H | Me | Cl | N | |
| 43 | CH$_2$CH$_2$SMe | CO—Me | — | H | Me | Cl | N | |
| 44 | Me | COOMe | — | H | Me | F | N | |
| 45 | CH$_2$C≡CH | " | — | H | Me | Cl | CH | |
| 46 | Me | " | 3-Me | H | Me | Cl | CH | |
| 47 | Me | " | 3-F | H | Me | Cl | CH | |
| 48 | Me | " | 3-NMe$_2$ | H | Me | Cl | CH | |
| 49 | Me | " | 6-F | H | Me | Cl | CH | |
| 50 | Me | " | 6-Cl | H | Me | Cl | CH | |
| 51 | Me | " | 3,6-Cl$_2$ | H | Me | Cl | CH | |
| 52 | Et | " | 3-Me | H | Me | Cl | CH | |
| 53 | Et | " | 3-F | H | Me | Cl | CH | |
| 54 | Et | " | 6-F | H | Me | Cl | CH | |
| 55 | Et | " | 6-Cl | H | Me | Cl | CH | |
| 56 | Et | " | 3-Me | H | Me | Cl | N | |
| 57 | Et | " | 6-F | H | Me | Cl | N | |
| 58 | $^n$Pr | " | — | H | Me | F | CH | |
| 59 | " | " | — | H | Me | F | CH | |
| 60 | $^i$Pr | " | — | H | Me | F | N | |
| 61 | " | " | 4-F | H | Me | Cl | CH | |
| 62 | " | " | 3-F | H | Me | Cl | N | |

Formulation examples a) A dusting powder is obtained by mixing 10 parts by weight of a compound of the formula (I) and 90 parts by weight of talc, as the inert substance, and comminuting the mixture in an impact mill.

b) A wettable powder which is readily dispersible in water is obtained by mixing 25 parts by weight of a compound of the formula (I), 64 parts by weight of kaolin-containing quartz, as the inert substance, 10 parts by weight of potassium ligninsulfonate and 1 part by weight of sodium oleoylmethyltauride, as the wetting and dispersing agent, and grinding the mixture in a pinned disk mill.

c) A dispersion concentrate which is readily dispersible in water is obtained by mixing 20 parts by weight of a compound of the formula (I) with 6 parts by weight of alkylphenol polyglycol ether (® Triton X 207), 3 parts by weight of isotridecanol polyglycol ether (8 EO) and 71 parts by weight of paraffinic mineral oil (boiling range, for example, about 255° to above 277° C.) and grinding the mixture to a fineness of less than 5 microns in a ball mill.

d) An emulsifiable concentrate is obtained from 15 parts by weight of a compound of the formula (I), 75 parts by weight of cyclohexanone, as the solvent, and 10 parts by weight of oxyethylated nonylphenol, as the emulsifier.

e) Water-dispersible granules are obtained by mixing 75 parts by weight of a compound of the formula (i), 10 parts by weight of calcium ligninsulfonate, 5 parts by weight of sodium lauryl sulfate, 3 parts by weight of polyvinyl alcohol and 7 parts by weight of kaolin, grinding the mixture on a pinned disk mill and granulating the powder in a fluidized bed by spraying on water as the granulating liquid.

f) Water-dispersible granules are also obtained by homogenizing and precomminuting 25 parts by weight of a compound of the formula (I), 5 parts by weight of sodium 2,2'-dinaphthylmethane-6,6'-disulfonate, 2 parts by weight of sodium oleoylmethyltauride, 1 part by weight of polyvinyl alcohol, 17 parts by weight of calcium carbonate and 50 parts by weight of water on a colloid mill, subsequently grinding the mixture on a bead mill and atomizing and drying the suspension thus obtained in a spray tower by means of a one-component nozzle.

Biological Examples

1. Action on weeds by the pre-emergence method

Seeds or pieces or rhizome of mono- and dicotyledon weed plants are laid out in sandy loam soil in plastic pots and covered with soil. The compounds according to the invention, formulated in the form of wettable powders or emulsion concentrates, are then applied to the surface of the covering soil as an aqueous suspension or emulsion in various dosages with an amount of water applied, when converted, of 600 to 800 l/ha.

After the treatment, the pots are placed in a greenhouse and are kept under good growth conditions for the weeds. The plant damage or emergence damage is rated visually after emergence of the test plants after a test period of 3 to 4 weeks in comparison with untreated controls. As the test results show, the compounds according to the invention have a good herbicidal pre-emergence activity against a broad spectrum of gramineous weeds and broad-leaved weeds. For example, compound No. 12 from Table 1 has a very good herbicidal action against harmful plants such as *Alopecurus myosuroides, Sinapis alba, Chrysanthemum segetum, Avena sativa, Stellaria media, Echinochloa crus-galli* and *Lolium multiflorum* when applied preemergence at a rate of 0.3 kg or less of active substance per hectare.

2. Action on weeds by the postemergence method

Seeds or pieces of rhizome of mono- and dicotyledon weeds are laid out in sandy loam soil in plastic pots, covered with soil and grown in a greenhouse under good growth conditions. Three weeks after sowing, the test plants are treated in the trifoliate stage.

The compounds according to the invention, formulated as wettable powders as emulsion concentrates, are sprayed onto the green parts of the plants in various dosages with an amount of water applied, when converted, of 600 to 800 l/ha. After the test plants have stood in the greenhouse under optimum growth conditions for about 3 to 4 weeks, the action of the preparations is rated visually in comparison with untreated controls. The compositions according to the invention also have a good herbicidal activity against a broad spectrum of economically important gramineous weeds and broad-leaved weeds in the postemergence method. For example, compound No. 12 from Table 1 has a very good herbicidal action against harmful plants such as *Alopecurus myosuroides, Sinapis alba, Stellaria media, Echinochloa crus-galli, Lolium multiflorum, Chrysanthemum segetum* and *Avena sativa* when applied postemergence at a rate of 0.3 kg or less of active substance per hectare.

3. Crop plant tolerance

In further tests in the greenhouse, seeds of a relatively large number of crop plants and weeds are laid out in sandy loam soil and covered with soil. Some of the pots are treated immediately as described under Section 1, and the others are placed in a greenhouse until the plants have developed two to three true leaves, and are then sprayed with the substances of the formula (I) according to the invention in various dosages as described under Section 2. Four to five weeks after the application and standing time in the greenhouse, it is found by visual scoring that the compounds according to the invention leave dicotyledonous crops, such as, for example, soya, cotton, oilseed rape, sugar beet and potatoes, undamaged by the pre- and postemergence method even at high dosages of active compound. Some substances, furthermore, also protect gramineous crops, such as, for example, barley, wheat, rye, sorghum-millet, maize or rice. For example, compound No. 12 from Table 1 has a very good selectivity in the postemergence method in crops such as wheat, maize and barley. The compounds of the formula (I) thus have a high selectivity when used for controlling unwanted plant growth in agricultural crops.

We claim:

1. A method for controlling harmful plants in crops of useful plants which comprises using as a selective herbicide a compound of the formula (I),

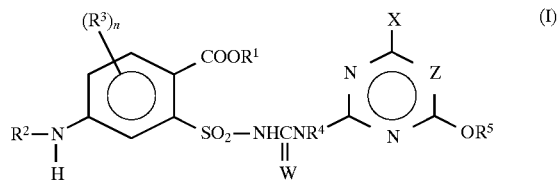

in which $R^1$ is H, $(C_1-C_6)$-alkyl, $(C_2-C_6)$-alkenyl, $(C_2-C_6)$-alkynyl, $(C_3-C_6)$-cycloalkyl, where the last four radicals mentioned are unsubstituted or substituted by one or more radicals from the group consisting of halogen, CN, $(C_1-C_3)$-alkoxy, $(C_1-C_3)$-haloalkoxy, unsubstituted and substituted $(C_3-C_6)$-cycloalkyl, $(C_1-C_3)$-alkylthio, $(C_1-C_3)$-alkylsulfinyl, $(C_1-C_3)$-alkylsulfonyl, unsubstituted phenyl, substituted phenyl, an unsubstituted heterocyclic radical and a substituted heterocyclic radical and, in the case of cyclic radicals, also $(C_1-C_4)$-alkyl and $(C_1-C_4)$-haloalkyl, or a heterocyclic radical having 3, 4, 5, 6 or 7 ring atoms and one or more atoms from the group consisting of O, N and S as hetero ring atoms, the radical being unsubstituted or substituted by one or more radicals from the group consisting of halogen, $(C_1-C_3)$-alkyl and $(C_1-C_3)$-haloalkyl, $R^2$ is an acyl radical, excluding formyl, $R^3$ is halogen, $(C_1-C_6)$-alkyl, $(C_1-C_6)$-alkoxy, $(C_1-C_6)$-haloalkyl, $(C_1-C_6)$-haloalkoxy, $NO_2$, CN, $NH_2$ or $(C_1-C_4)$-mono- or -dialkylamino, and in each case independently of other radicals $R^3$ if n is 2 or 3, $R^4$ is H or $(C_1-C_6)$-alkyl, $R^5$ is $(C_1-C_6)$-alkyl or $(C_1-C_6)$-haloalkyl, X is a halogen atom from the group consisting of F and Cl or halo-$(C_1-C_3)$-alkyl, n is 0, 1, 2 or 3, W is an oxygen atom or a sulfur atom and
Z is CH or N.

2. The method as claimed in claim 1, wherein, in formula (I), $R^1$ is $(C_1-C_6)$-alkyl, $(C_2-C_6)$-alkenyl, $(C_2-C_6)$-alkynyl, $(C_3-C_6)$-cycloalkyl, $(C_4-C_8)$-cycloalkyl-$(C_1-C_2)$-alkyl, phenyl-$(C_1-C_6)$-alkyl, where each of the last six radicals mentioned is unsubstituted or substituted by one or more radicals from the group consisting of halogen, CN, $OCH_3$, $OC_2H_5$, $OCF_3$, $SO_2CH_3$ and, in the case of cyclic radicals, also $(C_1-C_3)$-alkyl, or a radical of the formulae $A_1$ to $A_7$,

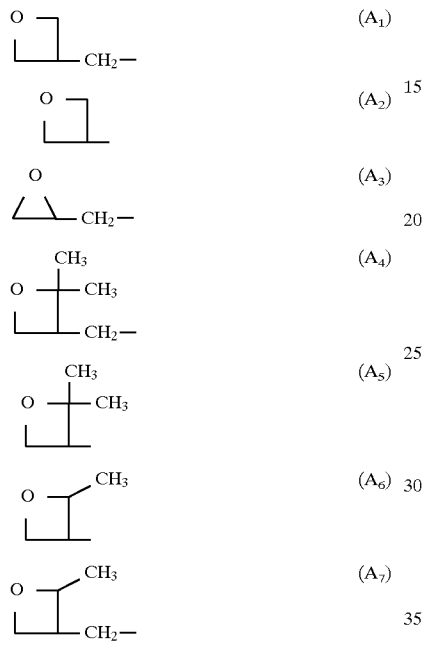

$R^2$ is $CO-R^6$, $CO-OR^7$, $CO-NR^8R^9$ or $SO_2-R^{10}$,
$R^3$ is halogen, $(C_1-C_3)$-alkyl, $(C_1-C_3)$-alkoxy, $(C_1-C_3)$-haloalkyl, $(C_1-C_3)$-haloalkoxy, $NO_2$, CN, $NH_2$, $NHCH_3$ or $N(CH_3)_2$,
$R^4$ is H or $(C_1-C_3)$-alkyl,
$R^5$ is $(C_1-C_3)$-alkyl or $(C_1-C_3)$-haloalkyl,
$R^6$ is $(C_1-C_6)$-alkyl, $(C_2-C_6)$-alkenyl, $(C_2-C_6)$-alkynyl, $(C_3-C_6)$-cycloalkyl, where each of the last four radicals mentioned is unsubstituted or substituted by one or more radicals from the group consisting of halogen, CN, $(C_1-C_4)$-alkoxy, $(C_1-C_4)$-haloalkoxy, mono-$(C_1-C_4)$-alkylamino, di-$(C_1-C_4)$-alkylamino, $(C_1-C_4)$-alkylsulfonyl, $(C_1-C_4)$-alkylsulfinyl, $[(C_1-C_4)$-alkoxy]carbonyl, aminocarbonyl, mono-$[(C_1-C_4)$-alkyl]aminocarbonyl, di-$[(C_1-C_4)$-alkyl]aminocarbonyl, phenyl and substituted phenyl, or phenyl, which is unsubstituted or substituted,
$R^7$ is a radical from the group of radicals possible for $R^6$,
$R^8$ and $R^9$ independently of one another are H, $(C_1-C_6)$-alkyl, $(C_2-C_6)$-alkenyl or $(C_2-C_6)$-alkynyl, where each of the last three radicals mentioned is unsubstituted or substituted by one or more radicals from the group consisting of halogen, CN, $(C_1-C_4)$-alkoxy, $(C_1-C_4)$-haloalkoxy, mono-$(C_1-C_4)$-alkylamino, di-$(C_1-C_4)$-alkylamino, $(C_1-C_4)$-alkylsulfonyl, $(C_1-C_4)$-alkylsulfinyl, $[(C_1-C_4)$-alkoxy]carbonyl, aminocarbonyl, mono-$(C_1-C_4)$-alkylaminocarbonyl and di-$[(C_1-C_4)$-alkyl]aminocarbonyl, or
$R^8$ and $R^9$, together with the N atom bonded to them, is an unsubstituted or substituted heterocyclic ring of four to eight ring atoms which, including the substituents, contains up to 18 carbon atoms, $R^{10}$ is $(C_1-C_5)$-alkyl or $(C_2-C_5)$-alkenyl, where each of the last two radicals mentioned is unsubstituted or substituted by one or more radicals from the group consisting of halogen, $(C_1-C_4)$-alkoxy, $(C_1-C_4)$-haloalkoxy, mono-$(C_1-C_4)$-alkylamino and di-$(C_1-C_4)$-alkylamino,
n is 0 or 1,
W is O,
x is F, Cl or $CF_3$, and
Z is CH or N.

3. The method as claimed in claim 1, wherein $R^1$ is $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_2)$-alkyl or phenyl-$(C_1-C_6)$-alkyl, where each of the last six radicals mentioned is unsubstituted or substituted by one or more radicals from the group consisting of halogen, CN, $OCH_3$, $OC_2H_5$, $OCF_3$, $SO_2CH_3$ and, in the case of cyclic radicals, also $(C_1-C_3)$-alkyl, or a radical of the formulae $A_1$ to $A_7$,

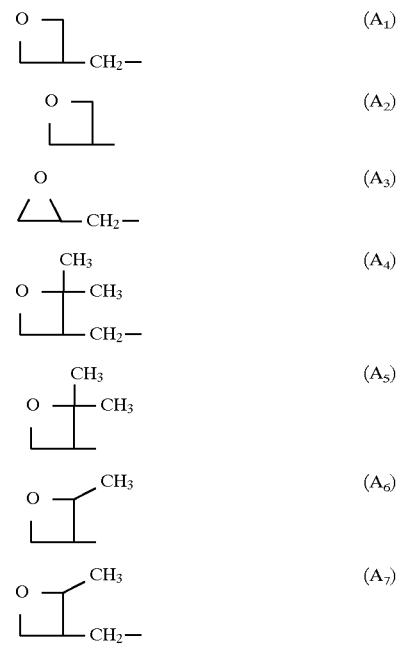

$R^2$ is $CO-R^6$, $CO-OR^7$, $CO-NR^8R^9$ or $SO_2-R^{10}$,
$R^3$ is halogen, $CH_3$, $C_2H_5$, $OCH_3$, $OC_2H_5$, $CF_3$, $CCl_3$, $OCF_3$, $OCHF_2$ or $N(CH_3)_2$,
$R^4$ is H or methyl,
$R^5$ is methyl, ethyl or $(C_1-C_2)$-haloalkyl,
$R^6$ is $(C_1-C_6)$-alkyl, $(C_2-C_6)$-alkenyl, $(C_2-C_6)$-alkynyl, $(C_3-C_6)$-cycloalkyl, where each of the last four radicals mentioned is unsubstituted or substituted by one or more radicals from the group consisting of F, Cl, Br, I, CN, $OCH_3$, $OCF_3$, $N(CH_3)_2$, $SO_2CH_3$, $CO_2CH_3$, $CON(CH_3)_2$ and phenyl,
or phenyl, which is unsubstituted or substituted up to three times by identical or different radicals from the group consisting of halogen, $CH_3$, $C_2H_5$, $OCH_3$, $OC_2H_5$, $CF_3$, $C_2H_5Cl$, $OCHF_3$ and $OCHF_2$,
$R^7$ is a radical from the group of radicals possible for $R^6$,
$R^8$ and $R^9$ independently of one another are H, $(C_1-C_6)$-alkyl, $(C_2-C_6)$-alkenyl or $(C_2-C_6)$-alkynyl, where each of the last three radicals mentioned is unsubstituted or substituted by one or more radicals from the group consisting of F, Cl, Br, CN, $OCH_3$, $OCF_3$, $N(CH_3)_2$, $SO_2CH_3$, $CO_2CH_3$ and $CON(CH_3)_2$, and
$R^{10}$ is $(C_1-C_4)$-alkyl or $(C_1-C_4)$-haloalkyl.

4. The method as claimed in claim 1, wherein $R^1$ is $(C_1-C_4)$-alkyl and $R^2$ is $CO-CH_3$, $CO-CH_2CH_3$, cyclopropylcarbonyl, isopropylcarbonyl, t-butylcarbonyl, $COOCH_3$, $COOC_2H_5$, $COOCH_2CH_2Cl$, $CONH_2$, $CONHCH_3$, $CO-NH-C_2H_5$, $CON(CH_3)_2$, $SO_2CH_3$, $SO_2C_2H_5$, $SO_2CH_2F$ or $SO_2CH_2Cl$.

5. The method as claimed in claim 4, wherein n is O, $R^4$ is hydrogen, $R^5$ is methyl, X is Cl, W is O and Z is CH.

6. The method as claimed in claim 5, wherein $R^1$ is methyl and $R^2$ is cyclopropylcarbonyl.

7. The method as claimed in claim 5, wherein $R^1$ is ethyl and $R^2$ is cyclopropylcarbonyl.

8. The method as claimed in claim 5, wherein $R^1$ is methyl and $R^2$ is $CO-CH_3$.

9. The method as claimed in claim 5, wherein $R^1$ is ethyl and $R^2$ is $CO-CH_3$.

10. The method as claimed in claim 5, wherein $R^1$ is methyl and $R^2$ is $CO-OCH_3$.

11. The method as claimed in claim 5, wherein $R^1$ is ethyl and $R^2$ is $CO-OCH_3$.

12. The method as claimed in claim 5, wherein $R^1$ is methyl and $R^2$ is $CO-OC_2H_5$.

13. The method as claimed in claim 5, wherein $R^1$ is methyl and $R^2$ is $CO-OC_2H_5$.

14. The method as claimed in claim 1, wherein the crop of useful plants is a cereal.

15. The method as claimed in claim 1, which comprises applying an active amount of at least one compound of the formula (I) to the plants, plant seeds thereof or the area on which the plants grow.

16. The method as claimed in claim 15, wherein the crop of useful plants is a cereal.

17. A herbicidal composition which comprises at least one compound of the formula (I) as set forth in claim 1 and formulation auxiliaries customary in plant protection.

* * * * *